US008868176B2

(12) United States Patent
Ludvig et al.

(10) Patent No.: US 8,868,176 B2
(45) Date of Patent: Oct. 21, 2014

(54) MICROELECTRODE-EQUIPPED SUBDURAL THERAPEUTIC AGENT DELIVERY STRIP

(75) Inventors: Nandor Ludvig, Richmond Hill, NY (US); Richard Rizzolo, Ukiah, CA (US); Hai M. Tang, Brooklyn, NY (US); Ruben I. Kuzniecky, Englewood, NJ (US); Werner K. Doyle, New York, NY (US)

(73) Assignee: New York University, New York, NY (US)

( * ) Notice: Subject to any disclaimer, the term of this patent is extended or adjusted under 35 U.S.C. 154(b) by 1131 days.

(21) Appl. No.: 12/506,638

(22) Filed: Jul. 21, 2009

(65) Prior Publication Data

US 2010/0179518 A1    Jul. 15, 2010

Related U.S. Application Data

(60) Provisional application No. 61/082,706, filed on Jul. 22, 2008.

(51) Int. Cl.
| | |
|---|---|
| A61N 1/30 | (2006.01) |
| A61B 5/00 | (2006.01) |
| A61M 5/172 | (2006.01) |
| A61B 5/04 | (2006.01) |
| A61M 5/142 | (2006.01) |
| A61B 5/0478 | (2006.01) |
| A61M 39/02 | (2006.01) |

(52) U.S. Cl.
CPC ............. *A61B 5/0478* (2013.01); *A61B 5/4839* (2013.01); *A61M 2039/0211* (2013.01); *A61M 2205/50* (2013.01); *A61M 5/1723* (2013.01); *A61B 2560/063* (2013.01); *A61B 5/04001* (2013.01); *A61M 2205/3523* (2013.01); *A61M 2202/0464* (2013.01); *A61B 2562/043* (2013.01); *A61M 5/14276* (2013.01); *A61M 2230/10* (2013.01); *A61B 2562/046* (2013.01); *A61B 5/4094* (2013.01); *A61M 2210/0693* (2013.01); *A61B 5/6882* (2013.01); *A61B 2562/0209* (2013.01)
USPC ............................................ 604/21; 604/173

(58) Field of Classification Search
USPC ......... 604/20, 21, 66, 173, 503, 890.1, 891.1; 606/544, 545; 600/544, 545
See application file for complete search history.

(56) References Cited

U.S. PATENT DOCUMENTS

| | | | |
|---|---|---|---|
| 6,497,699 B1 | 12/2002 | Ludvig et al. | |
| 2003/0083645 A1* | 5/2003 | Angel et al. | ................ 604/890.1 |
| 2005/0113744 A1* | 5/2005 | Donoghue et al. | .............. 604/66 |
| 2007/0060973 A1 | 3/2007 | Ludvig et al. | |
| 2008/0229672 A1* | 9/2008 | Woo et al. | ........................ 51/295 |
| 2010/0056900 A1* | 3/2010 | Whitcomb et al. | ........... 600/414 |

* cited by examiner

*Primary Examiner* — Kami A Bosworth
(74) *Attorney, Agent, or Firm* — Fay Kaplun & Marcin, LLP

(57) ABSTRACT

An apparatus for treating the brain, comprises a first fluid delivery device including a distal end sized and shaped for placement at a first target site between a dura mater and a pia mater of the brain, the first fluid delivery device including a first fluid lumen extending to a first outlet port in the distal end to deliver fluids to a first target location and a first microelectrode mounted within the distal end of the first fluid delivery device for movement between an insertion position in which a first distal tip of the first microelectrode is received within the first fluid delivery device and a deployed position in which the first microelectrode extends out of the first fluid delivery device with the first distal tip thereof penetrating the pia mater to a first electrode target position in the cerebral cortex.

24 Claims, 7 Drawing Sheets

MICROELECTRODE-EQUIPPED SUBDURAL THERAPEUTIC AGENT DELIVERY STRIP

PRIORITY CLAIM

This application claims the priority to the U.S. Provisional Application Ser. No. 61/082,706, entitled "Microelectrode-Equipped Subdural Therapeutic Agent Delivery Strip," filed on Jul. 22, 2008. The specification of the above-identified application is incorporated herewith by reference.

BACKGROUND

The present invention relates generally to systems and methods for treating brain disorders. More specifically, the present invention relates to a system and method for monitoring and responding to cellular electrophysiological changes in the brain corresponding to disorders originating primarily in the neocortex but also in other regions including the spinal cord. This invention builds on the applicants' prior patent entitled "Hybrid neuroprosthesis for the treatment of brain disorders" now issued as U.S. Pat. No. 6,497,699 and another prior patent entitled "Apparatus and Method for Monitoring and Treatment of Brain Disorders" currently pending as U.S. Patent Publication Number 2007/0060973 the entire disclosures of which are hereby expressly incorporated herein by reference.

As known to those skilled in the art, neural activity within the brain may be influenced through direct application of therapeutic agents to the brain. While EEG technology remains invaluable for short term diagnosis of epilepsy and automatic seizure detection, its limitations have become evident, particularly in reference to long-term diagnoses and treatments. Long term analysis and treatment of identified single neurons is not currently a realistic goal because the slightest movement (i.e., 40-80 µm) of an electrode away from a recorded cell (e.g., due to cerebrovascular pulsation) abruptly ends the recording.

SUMMARY OF THE INVENTION

The present invention is directed to an apparatus for treating the brain, comprising a first fluid delivery device including a distal end sized and shaped for placement at a first target site between a dura mater and a pia mater of the brain, the first fluid delivery device including a first fluid lumen extending to a first outlet port in the distal end to deliver fluids to a first target location and a first microelectrode mounted within the distal end of the first fluid delivery device for movement between an insertion position in which a first distal tip of the first microelectrode is received within the first fluid delivery device and a deployed position in which the first microelectrode extends out of the first fluid delivery device with the first distal tip thereof penetrating the pia mater to a first first electrode target position in the cerebral cortex.

DETAILED DESCRIPTION

Figure 1:
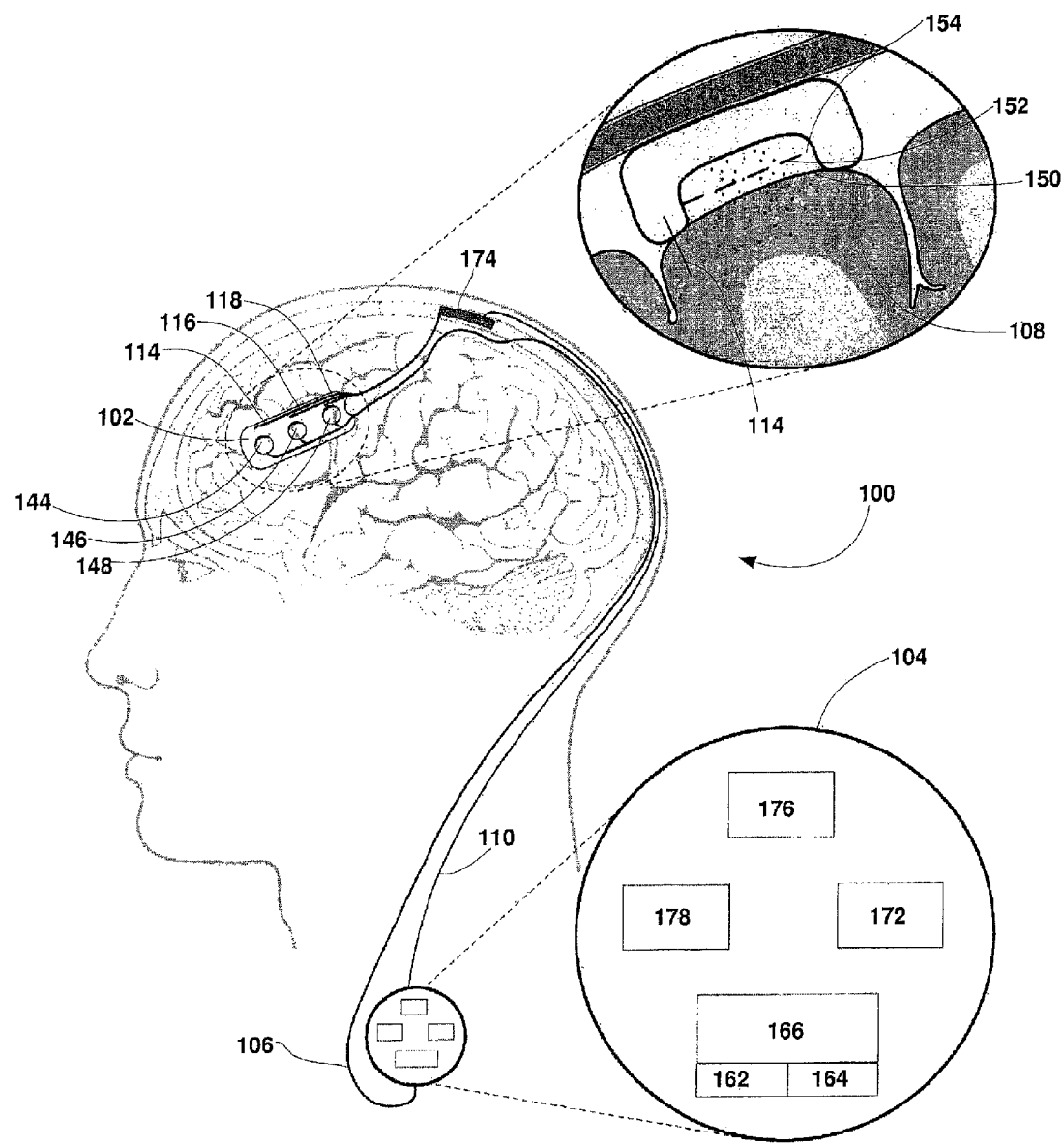
FIG. 1 shows an exemplary embodiment of a subdural system according to the present invention.

The present invention may be further understood with reference to the following description and the related appended drawings, wherein like elements are provided with the same reference numerals. The present invention describes a system combining pharmacological and electrophysiological instruments for the treatment of brain disorders. A system in accordance with the present invention includes a sensing device and a subdural therapeutic agent delivery device for implantations in a subdural space. Exemplary embodiments of the present invention employ direct neuronal recordings in order to provide a more promising way to capture fine electrophysiological signals to predict epileptic seizures. Neuron recording offers an efficient way to adjust intracranial therapies to the dynamic changes in cortical tissue function following stroke and other focal diseases as well. Multi-neuronal recording according to the present invention, coupled with the localized deliveries of therapeutic agents, is an ideal method for the long-term management of otherwise untreatable focal neocortical disorders, including epilepsy and some forms of stroke and tumor. Coupling of multi-neuron recording microelectrodes with an apparatus capable of delivering therapeutic agents to the recorded area thus creates the opportunity to monitor, treat and potentially cure diseased neural tissue.

In one respect as described in more detail below, the present invention is directed to a system and method for both effectively monitoring multi-neuronal brain activity over an extended period of time (e.g., a month or more) in diseased areas and delivering therapeutic agents into the same areas to provide treatment. An exemplary system according to the present invention comprises one or more subdural delivery strips, each connected by a catheter to a subcutaneously implanted device to sense imbalances in electrical activity of a target area of the brain and provide a therapeutic agent thereto to correct the abnormal brain electrical activity. Specifically, electrodes of each subdural delivery strip are inserted into the cerebral cortex to detect electrical activity of multiple neurons and/or neuron-populations. Alternatively and/or additionally, a neurochemical sensor (and/or any other device capable of detecting data corresponding to activity of a selected area of the brain (e.g., blood flow)) may be deployed from one or more of the subdural delivery strips to detect chemical activity (e.g., glutamate release) or a chemical state (e.g., extracellular glucose level) of the target area. All detected neurological data is then transmitted for analysis to a subcutaneous device implanted, for example, in the thoracic cavity. Upon the detection of one or more predetermined abnormal patterns in the neurological data, the subcutaneously implanted device directs a pump contained therein to deliver one or more therapeutic agents to the target areas of the brain via the various subdural delivery strips. The exemplary embodiment of the present invention is particularly useful for individuals for whom traditional treatments for brain disorders have been either ineffective due to, for example, inadequate response to systemically applied therapeutic agents or nonviable due to, for example, risk factors associated with surgical intervention.

As shown in FIGS. 1-8, a system 100 for sensing brain activity and delivering therapeutic agents to target locations of the brain includes a plurality of subdural delivery strips 102, each extending from a distal end at a target site between the dura mater and the pia mater of a brain 108 to a proximal end comprising a subcutaneous device 104. In this embodiment, a proximal end of each of the subdural delivery strips 102 is coupled to a catheter 106 which extends to a subcutaneous device 104. The catheter 106 may be a dual-lumen catheter formed of a flexible biocompatible material wherein each of the lumens thereof may delivery a different fluid to a target area of the brain 108, as will be described in greater detail below. In an exemplary embodiment, each subdural delivery strip 102 is inserted into the brain 108 with a distal end thereof extending past the dura mater and arachnoid mater to lie upon the pia mater abutting the cerebral cortex, as those skilled in the art will understand. Placement of the subdural delivery strips 102 in this manner facilitates the delivery of a plurality of micro-electrodes 114, 116, 118 to obtain multi-neural activity readings from the brain 108 while minimizing noise. Each of the subdural delivery strips 102 according to the present invention is adapted to record action potentials of multiple neurons (e.g., 20 or more) from the same brain area. Furthermore, a subdural delivery also for a delivery of therapeutic agents to targeted subdural areas without significant spillover to neighboring areas, as will be described in greater detail below.

Figure 2:
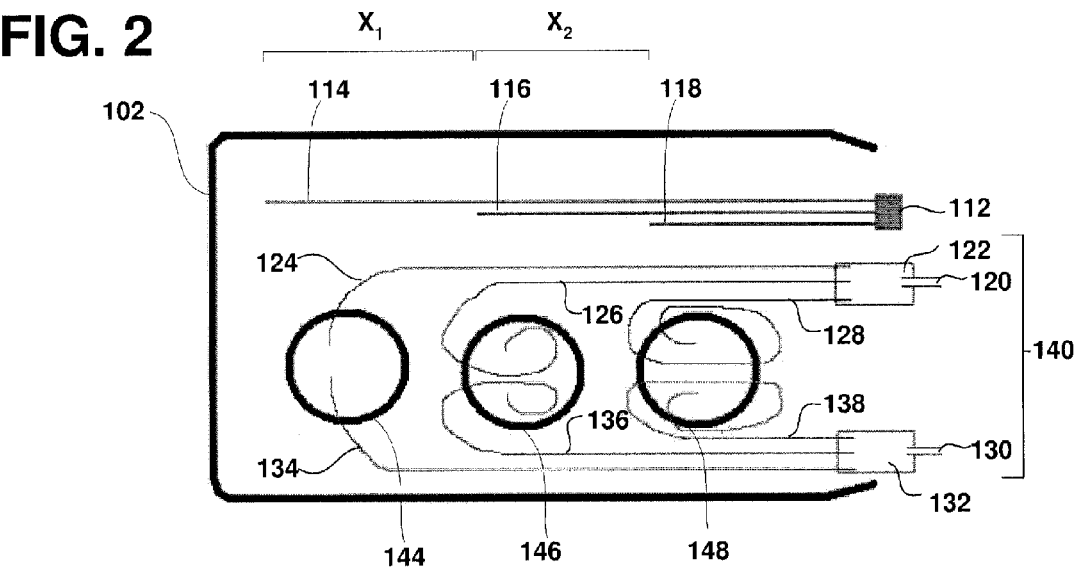
FIG. 2 shows a detailed view of the subdural strip of FIG. 1.

As would be understood by those skilled in the art, the placement of the subdural delivery strips 102 may be selected depending on the pathology of the patient, the brain areas evincing abnormal activity, etc. The subdural delivery strips 102 each comprise a plurality of microelectrodes 114, 116, 118 housed within a canal 142 coated with, for example, a material such as Teflon or fused silica for reducing friction between the wall of the canal 142 and the advancing microelectrode so that the microelectrodes can be moved easily. Specifically, the canal 142 extends through the subdural delivery strip 102 and opens to a distal face thereof, as shown in FIG. 2. Each of the microelectrodes 114, 116, 118 may be made, for example, of nichrome and preferably has a diameter of approximately 50-100 Ym. Furthermore, each of the individual microelectrodes 114, 116, 118 is formed with a different length with a difference $X_1$, $X_2$ between adjacent microelectrodes 114, 116, 118 being defined so that, when inserted into the cerebral cortex, distal ends of the individual microelectrodes 114, 116, 118 are laterally spaced from one another by the predetermined distance. Those skilled in the art will understand that the difference $X_1$, $X_2$ between adjacent electrodes may be varied based on the conditions of the patient. The plurality of microelectrodes 114, 116, 118 allows for the monitoring of neural activity of substantially an entire abnormal area of the brain (e.g., an area associated with epilepsy).

The subdural delivery strips 102 further comprise a therapeutic agent delivery pump 166 comprising a first outlet 120 and a second outlet 130 each coupled to the subcutaneous device 104 for monitoring and analyzing activity of the brain and for delivering fluids based on these electrical signals. Specifically, the first outlet 120 delivers a fluid such as artificial cerebrospinal fluid (ACSF) to flush the strips 102 clean (i.e., to clear material which has entered the distal end of the strips 102) at regular intervals or when a clogged condition is detected while the second outlet 130 (not shown) is coupled to a source of one or more therapeutic agents (e.g., anti-siezure medication) for supply to the target area of the brain upon detection of specific brain activity (e.g., pathological brain activity or brain activity indicating that pathological activity such as a seizure is imminent). In the exemplary embodiment shown, each of the first and second outlets 120, 130 is coupled to three tubes 124, 126, 128 and 134, 136, 138, respectively, wherein each tube 124, 126, 128 extends therefrom to a respective one of fluid delivery ports 144, 146 148. It is further noted that any number of such tubes and delivery ports may be employed without deviating from the spirit and scope of the present invention.

A single subdural delivery strip 102 may comprise, for example, 3-8 delivery ports 144, 146, 148, each with a diameter of approximately 5-20 mm. allowing the treatment of cortical areas ranging from 1-8 $cm^2$. However, depending on the number of distinct, dysfunctional cortical areas and the size of each of these areas, multiple strips can be preferably inserted in the subdural space 108 instead of a single strip (e.g., in the case of epilepsy with multiple seizure foci). In this manner, several subdural delivery strips 102 may be placed over seizure foci located in one or more of the frontal, temporal and occipital lobes to record and treat each and every epileptogenic zone.

The first outlet 120 includes three first tubes 124, 126 and 128 extending therefrom to the delivery ports 144, 146 and 148, respectively, while the second outlet 130 includes three second tubes 134, 136 and 138 extending therefrom to the delivery ports 144, 146 and 148, respectively. Each of the first tubes 124, 126, 128 is equal in length to one another. The tubes 126 and 128 opening to the more proximal ports 146, 148, respectively, follow a slightly winding path with the equal path length ensuring simultaneous delivery of substantially equal quantities of fluid via each of the ports 144, 146, 148. Similarly, the second tubes 134, 136 and 138 are also equal in length to one another following, for example, similarly winding paths to achieve the same path length ensuring the same simultaneous delivery of equal quantities of fluids from each of the ports 144, 146, 148. Specifically, the same time is required for a fluid to travel from the first port (not shown) to the delivery ports 144, 146, 148. Similarly, the same time is required for fluids to travel from the second port (not shown) to each of the delivery ports 144, 146, 148. This prevents a situation where proximal treatment areas receive a greater volume of fluid than desired while more distal areas receive a lesser volume of fluid than desired.

In this embodiment, distal portions of the first tubes 124, 126 and 128 are placed adjacent to one another while the second tubes 134, 136 and 138 also extend adjacent to one another, as shown in FIG. 2. Each of the three delivery ports 144, 146 and 148 lies along a plane of a corresponding one of the microelectrodes 114, 116 and 118 (when in a deployed position) so that regions receiving fluids from these delivery ports 144, 146, 148 is associated with the electrical activity detected by the microelectrodes 114, 116, 118.

Premature leakage from each first tubes 124, 126, 128 and second tubes 134, 136, 138 is prevented by a laser-perforated disk 152 situated over each of the therapeutic agent delivery ports 142, 144 and 148. Each of the laser-perforated disks 152 is preferably formed of a biocompatible material and more specifically, of an MRI-compatible material such as platinum and has approximately 5,000-60,000 perforations with each perforation having a diameter of approximately 4-6 µm. and separated from an adjacent perforation by approximately 10-30 Ym. In a preferred embodiment, the laser-perforated disk 152 comprises a diameter of 5 mm. and comprises 31,000 perforations therein. The perforations 154 are adapted to permit efficient fluid outflow while preventing clogging of the therapeutic agent delivery ports 144, 146, 148 by blood clots and tissue debris, etc. Specifically, the perforations 154 may, for example, be formed by laser pulses, but may alternatively be formed by mechanical means such as piercing or cutting. The disk 152 further comprises a silicone rim 156 for engaging the pia mater to provide a space between the pia mater and the disk 152 preventing spillover of the fluids delivered via the ports 144, 146, 148 into neighboring areas of the brain.

The first outlet 120 and second outlet 130 are fluidly connected via the catheter 106 to a dual-chamber reservoir 164 located within the therapeutic agent delivery pump 166. The reservoir 164 may be fluidly coupled to or located in the subcutaneous device 104 implanted in the body (e.g., in the thoracic cavity, etc.). For example, the reservoir 164 may be housed in a multi-chambered storage device implanted subcutaneously and may contain separate chambers for the storage of different fluids. A dual-lumen catheter 106 may pass from the subcutaneous device 104 under the skin past the neck and under the scalp to the craniotomy. The catheter 106 enters the skull 170 via the craniotomy with a first lumen of the catheter 106 coupling to the first outlet 120 while a second lumen of the catheter 106 couples to the second outlet 130. Those skilled in the art will understand that the drug delivery strips 102 may be integrally formed with the catheter 106 if desired. The subcutaneous device 104 may be constructed for implantation with at least a proximal portion 162 thereof accessible through the skin allowing for refilling of the reservoir 164 through the skin. For example, the accessible portion 162 may include a self-sealing septum, as is known in the art, capable of retaining an airtight seal even after numerous penetrations by a syringe or other access device. The accessible portion 162 of the reservoir 164 may also contain markings or other identifying indicia as is known in the art facilitating discrimination of each chamber (not shown) of the dual-chamber reservoir 164 from one another so that the desired fluids may be accurately delivered to the desired one thereof.

The microelectrodes 114, 116, 118 are coupled to the subcutaneous device 104 via a wired connection (e.g., embedded in a wall of the catheter 106). Alternatively or additionally, as would be understood by those skilled in the art, the microelectrodes 114, 116, 118 may be coupled to the subcutaneous device 104 and/or to an external control apparatus (e.g., a computer) via a wireless connection. The subcutaneous device 104 itself may also be wirelessly coupleable to an external computer if desired. The subcutaneous device 104 also includes a subcutaneously disposed power supply 172, which, in a preferable embodiment, is transcutaneously rechargeable to power the subcutaneous device 104 for an extended period of time without being physically accessed or replaced. Alternatively, any suitable known non-rechargeable power source may be used.

The subcutaneous device 104, which receives a signal first processes through a signal conditioner 174 located external thereto, comprises a microprocessor 176, and an RF communication module 178. The signal conditioner 174 is coupled to the catheter 106 of the subdural delivery strips 102 for the receipt of input therefrom and serves to filter, amplify, and convert the signal to a new form (e.g., analog-to-digital) and transmits the resulting signal to the microprocessor 176 of the subcutaneous device 104. However, the step of converting the analog signals to digital signals as well as the signal conditioning may be performed by the microprocessor 176 itself if, for example, the microprocessor 176 comprises a built in amplifier, filter and analog to digital converter.

As described above, the subcutaneous device 104 may also comprise one or more pumps 166 electrically controlled by detected brain activity (e.g., analysis of neural readings provided by the subdural delivery strip(s) 102). The pump 166 may, for example, be a miniature, dual peristaltic pump allowing the alternating or simultaneous delivery of fluids from the reservoir 164. For example, a first chamber (not shown) of the reservoir 164 may include ACSF which may be supplied to the first outlet 120 while a second chamber (not shown) of the reservoir 164 includes a solution of a therapeutic agent which may be supplied to the second outlet 130 via the catheter 106. Alternatively, the pump 166 may be a piezoelectric pump, osmotic pump, an electromagnetic pump or other electrically controllable device for supplying fluid to the subdural delivery strips 102. In an alternate embodiment, each chamber of the reservoir 164 may be coupled to a separate pump. Furthermore, each chamber of the reservoir 164 may be connected to a plurality of catheters instead of a single dual-lumen catheter 106. Still further, the reservoir 164 may be a single chambered reservoir, wherein at least two separated reservoirs may be employed to house two separate fluids in accordance with the present invention. It will be appreciated that the components of the subcutaneous device 104 of the present invention may be implanted at any of a variety of locations throughout the body together or located separately as desired. In an alternate embodiment, the subcutaneous device 104 may be located outside the body.

Figure 3:
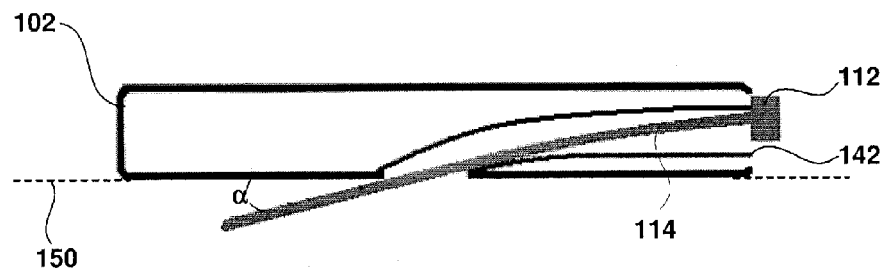
FIG. 3 shows a sagittal cross-sectional view of a subdural strip of FIG. 1.
Figure 4:
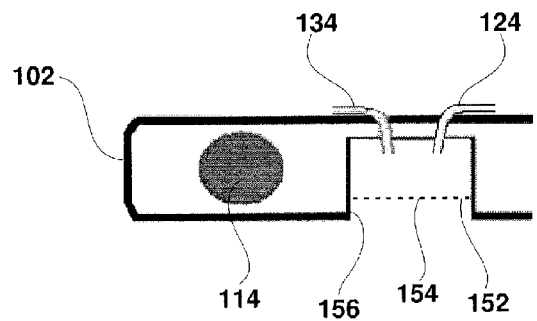
FIG. 4 shows a frontal cross-sectional view of a subdural strip of FIG. 1.
Figure 5:
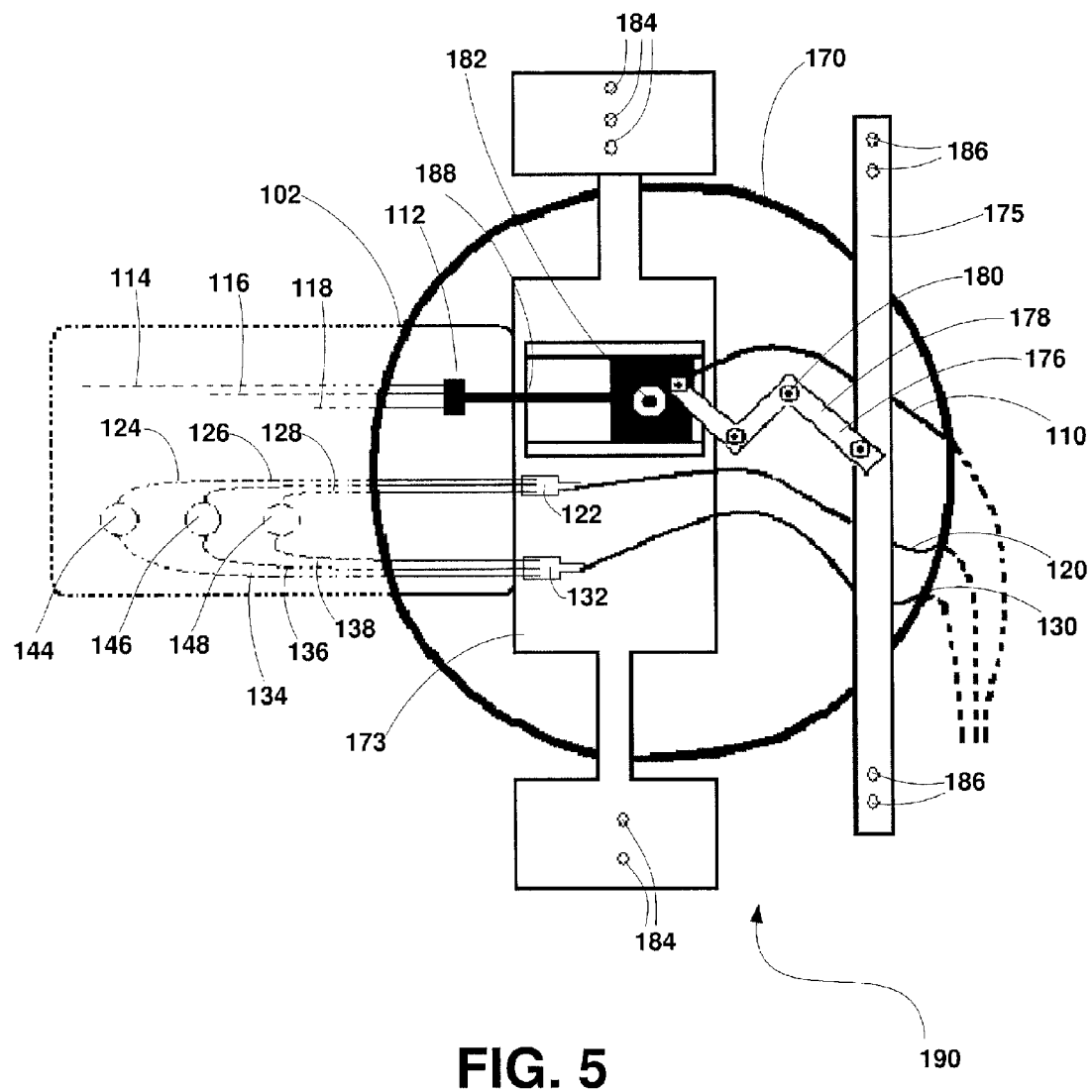
FIG. 5 shows a top view of the subdural strip of FIG. 1, as placed in a craniotomy.
Figure 6:
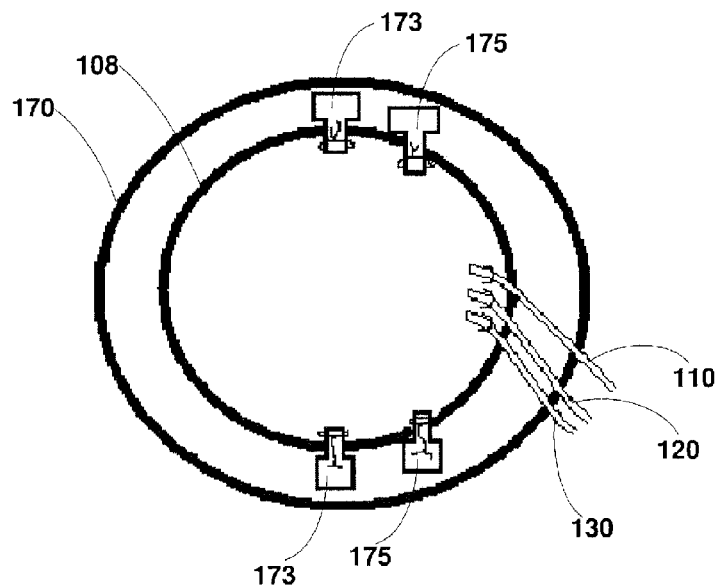
FIG. 6 shows a partial top view of the subdural strip of FIG. 1 covered with dura mater.
Figure 7:
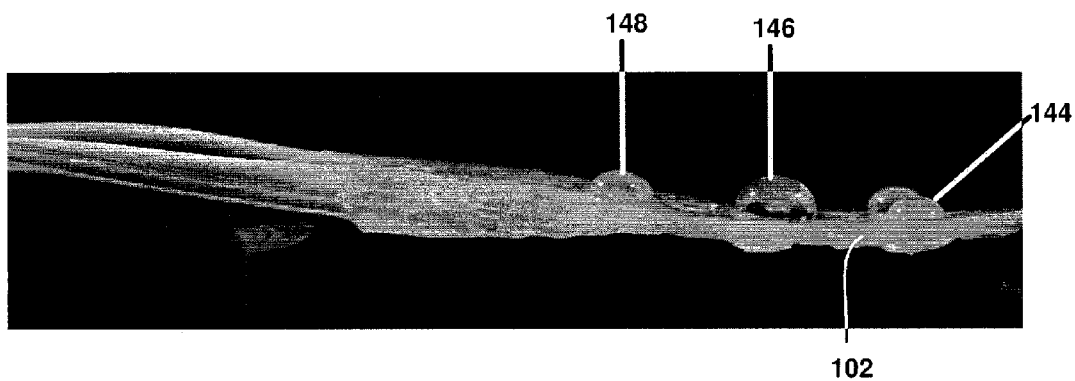
FIG. 7 shows a lateral view of the subdural strip of FIG. 1.

FIGS. 5 and 6. depict an assembly 190 used to perform an exemplary method according to the present invention. Initially, a craniotomy procedure is performed to remove a portion of the skull 170 and provide direct access to the brain 108, as shown in FIGS. 1, 5 and 6. One or more subdural delivery strips 102 are then inserted through the dura mater and arachnoid mater to rest directly on a target portion of the superficial cortical surface 150 (i.e., the pia mater), as shown in FIG. 3, and held in place by pressure applied thereto by the overlying dura mater and arachnoid mater. Each subdural delivery strip 102 is inserted in a positioning configuration in which the microelectrodes 114, 116, 118 are withdrawn proximally so that distal ends thereof are received inside the Teflon or fused silica canal 142. Once the subdural delivery strip 102 has been advanced to a target position adjacent the cortical surface 150, a bridge 173 (formed, for example, of silicone) is attached to an unremoved portion of the skull 170. Screws 184 located on proximal and distal ends of the bridge 173 are screwed into the skull 170 to maintain a position thereof. As would be understood by those skilled in the art, a location of the bridge 173 is preferably chosen to lie in proximity to the treatment area comprising the subdural delivery strip 102. A bridge 174 (formed, for example, of platinum) is then placed over the skull 108 and attached thereto via a series of screws 186 screwed thereinto. The bridge 174 is spaced from the bridge 173 by a distance sufficient to contain an microelectrode-advancing mechanism 176 therebetween. The microelectrode-advancing mechanism 176 comprises a plurality of arms 178 connected to one another at ends comprising joints 180 that permit rotational movement of the arms 178 with respect to one another. At one end, the microelectrode-advancing mechanism 176 is attached to the bridge 174 and, at an opposite end, to the bridge 173. Specifically, a distal portion of the microelectrode-advancing mechanism 176 is connected to a proximal end of a rod 188, which, at a distal end, is connected to the connector pin 112. The microelectrodes 114, 116, 118 are then advanced out of the canal 142 and into the target portion of the brain 108 manually by straightening the arms 178 of the microelectrode-advancing mechanism 176, thus lengthening the microelectrode-advancing mechanism 176 and exerting a pressure on the rod 188 and the connector pin 112. The pressure is translated to the microelectrodes 114, 116, 118, pushing them out of the canal 142 and into the brain 108. Once the microelectrodes 114, 116, 118 reach target sites in the brain 108, a tightening screw 182 is turned to squeeze the rod 188 to the first bridge 173, thus locking the microelectrodes 114, 116, 118 in position.

The microelectrodes 114, 116, 118 are extended distally out of the canal 142 of the subdural delivery strip 102 to penetrate the cerebral cortex at an angle α of approximately 10-30 degrees to a depth of approximately 0.5-2.0 mm. below the superficial cortical surface 150. CSF from the subdural/subarachnoid space can enter into the canal 142 and exit therefrom at a proximal opening receiving the microelectrodes 114, 116, 118 therein, as shown in FIG. 2. The flow of CSF through the canal 142 does not affect the recording ability of the subdural delivery strip 102, as the connections between the microelectrodes 114, 116, 118 and both the signal conditioner 174 and the subcutaneous device 104 are fluidly sealed by the closed dura mater, as depicted in FIG. 6. The angular configuration of the canal 142 permits microelectrodes 114, 116, 118 to exit therefrom only at the appropriate angle α. Furthermore, each of the microelectrodes 114, 116, 118 is preferably formed of a length to ensure penetration to no more than a maximum desired distance (e.g., 0.5 to 1.0 mm.) below the cortical surface. For example, the microelectrode 114 may progress to a depth of approximately 1.0 mm. while the microelectrode 118 may only approach a depth of approximately 0.5 mm. because of its shorter length with the electrode 116 penetrating by 0.75 mm. In this manner, distal ends of each of the individual microelectrodes 114, 116, 118 rest in different portions of the cerebral cortex. However, if desired, the microelectrodes 114, 116, 118 may penetrate into the cortical tissue at equal depths.

Once each of the microelectrodes 114, 116, 118 has reached a target portion of the brain 108, they are locked in place by turning the tightening screw 182 to prevent any movement of the microelectrodes 114, 116, 118 in relation to the first bridge 173 and the skull 170. Subsequently, a second bridge 175 and the microelectrode-advancing mechanism 176 are no longer needed and thus separated from first bridge 173 and removed from the craniotomy. Powered by the power supply 172, each of the individual microelectrodes 114, 116, 118, connected at proximal ends thereof to a corresponding connector pin 112 records multi-neuron activity from the target site via a separate recording channel. Accordingly, each microelectrode 114, 116, 118 is able to record multi-neuronal activity from the cerebral cortex and to record EEG signals as well. As described above signals from the microelectrodes 114, 116, 118 are transmitted to the signal conditioner 174 and the subcutaneous device 104 via an electrical pathway 110 (e.g., a wire). It is noted that although the electrical pathway 110 is depicted following a path separate from the catheter 106, the pathway 100 may extend through or along the catheter 106 as would be understood by those skilled in the art.

The second bridge 175 and the microelectrode-advancing mechanism 178, which are only temporarily needed for the craniotomy, are now removed from the assembly 190 and the dura mater of the brain 108 is sutured. The first and second outlets 120, 130 and the electrical pathway 110 may then be connected to the assembly 190 and the craniotomy closed. It is noted that although the first and second outlets 120, 130 are shown following separate paths, they may follow a common path (e.g., along the catheter 106 as would be understood by those skilled in the art. The catheter 106 is passed under the skin of the scalp, the neck and the back using known methods to a target body cavity (e.g., the thoracic cavity) in which the subcutaneous device 104 has been or will be implanted using known methods. Proximal ends of the lumens of the catheter 106 are then connected to the subcutaneous device 104 (e.g., to the reservoir 164 thereof).

Upon receiving neurological activity readings from the plurality of microelectrodes 114, 116, 118, the microprocessor 176 determines whether an abnormality is present according to a method known in the art such as, for example, a method disclosed in U.S. Patent Publication Number 2007/0060973 entitled "Apparatus and Method for Monitoring and Treatment of Brain Disorders" to Ludvig et al., the entire contents of which are included herein by reference. The received signals (e.g., analog electrophysiological signals from a neuron-population) are then conditioned by the signal conditioner 174, which, for example, filters, amplifies, and converts the signal to a new form (e.g., analog-to-digital). Specifically, the neurological activity readings are transmitted to the microprocessor 176, which converts the analog signals to digital signals. As discussed previously, the microprocessor 176 may also perform signal conditioning on the neurological activity readings.

The microprocessor 176 preferably includes one or more of a digital signal processor (DSP), a programmable logic array (PLA), an application-specific integrated circuit (ASIC), and a field-programmable gate array (FPGA) for analyzing in real-time signals received from the signal conditioner 174 to determine the presence of abnormal brain activity associated with brain disorders (or with a specific brain disorder) or to detect the onset of specific brain dysfunctions. Of course, those skilled in the art will understand that any number of other devices may be suitable to perform the functions of the microprocessor 176. Based on the results of this determination, the microprocessor 176 operates the therapeutic agent delivery pump 166 to treat the detected condition by the application of therapeutic fluids to and/or the removal of fluids from selected target areas of the brain at which the subdural delivery strips 102 have been mounted. Signal transfer between the microprocessor 176 and each of the subdural delivery strips 102 and between the microprocessor 176 and the therapeutic agent delivery pump 166 may be accomplished via a series of buses (not shown), as those skilled in the art will understand. The microprocessor 176 may also maintain regular deliveries of cleansing fluid through the catheter 106 and control functions of the power supply 172 and the RF communication module 178. Optionally, it may be desirable to allow the patient to assume control of the system under certain conditions. For example, if the patient feels a seizure coming on that has not been detected by the system, he may transmit a signal to the microprocessor 176 ordering immediate delivery of a dosage of a therapeutic fluid to a target area of the brain. Alternatively, the patient's indication that symptoms are present (e.g., a seizure is coming on) may be used by the microprocessor 176 to learn patient-specific EEG patterns that may be used to improve the system's ability to detect the brain activity corresponding to the symptom.

Figure 8:
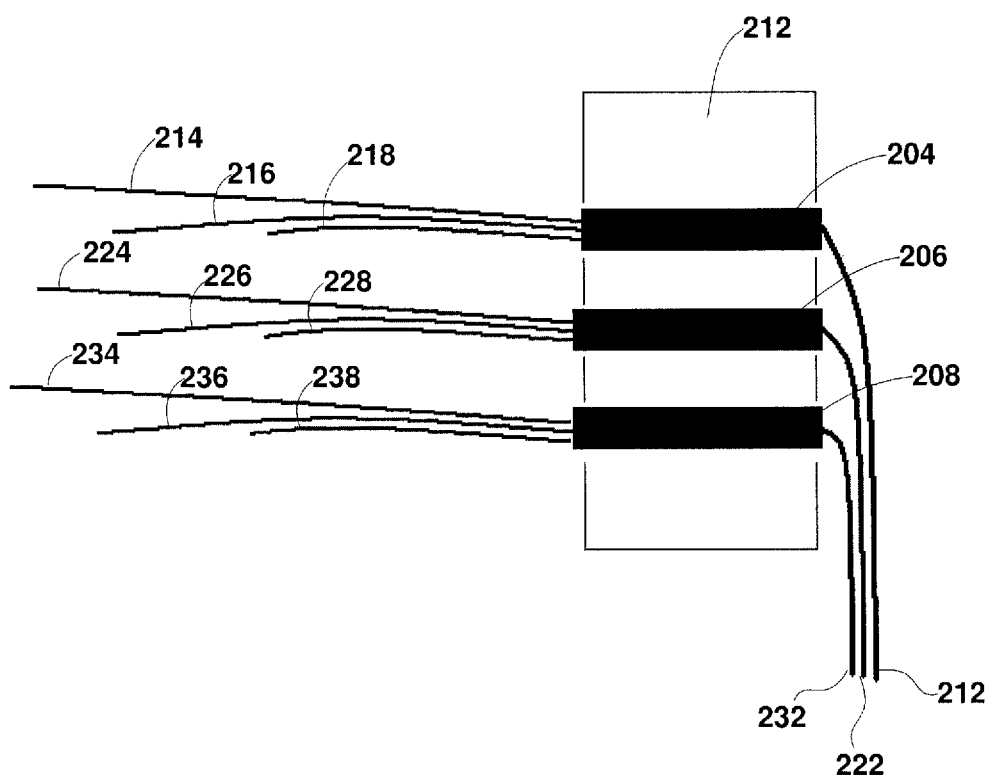
FIG. 8 shows a top view of a microelectrode for a subdural strip according to a second exemplary embodiment of the present invention.

In an alternate embodiment of the present invention, as shown in FIG. 8, a multi-branch microelectrode apparatus 212 may be employed including a plurality of connector pins such as, for example, pins 204, 206 and 208 housed therein. Each of the connector pins may be coupled to more than one microelectrode. In one example, each of the connector pins 204, 206, 208 is coupled to three microelectrodes 214, 216, 218; 224, 226, 228; and 234, 236, 238, respectively. In this manner, electronic readings may be taken for a multitude of different portions of the brain 108 without the need for multiple subdural delivery strips 102. Furthermore, it is noted that, in an exemplary embodiment, the number of fluid delivery ports in this embodiments may be equivalent to the number of microelectrodes so that a target fluid may be properly supplied to each reading area.

In determining whether an abnormality is present, normative data corresponding to the activity of selected portions of the brains of individuals who exhibited symptoms of a specific brain disorder (e.g., norms determined from comparisons of a population of individuals suffering from a disorder to control data) may be compared to the activity in the corresponding portions of the brain of the patient to determine whether the detected activity indicates the presence of the disorder or specific brain dysfunctional brain activity associated with that disorder. Based on the type of disorder detected, the microprocessor 176 is pre-programmed to immediately administer a predetermined dose of a predetermined therapeutic agent to the target area of the brain. By administering the dosage immediately upon detection of abnormal activity, the microprocessor 176 effectively prevents the onset of symptoms (i.e., seizures) of the brain dysfunction. Specifically, studies have proven that neurological data serves as an acceptable means of predicting the onset of symptoms associated with a brain dysfunction.

Figure 9A:
FIG. 9A shows normal EEG readings from a rat subject taken over a long term period via the method according to the present invention.
Figure 9B:
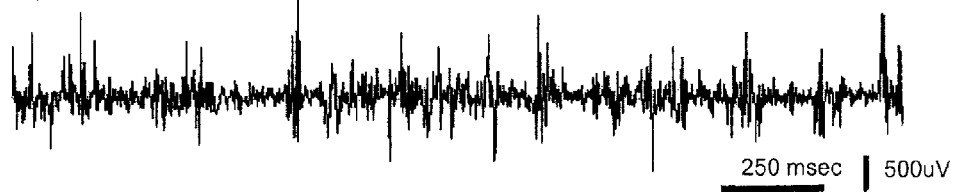
FIG. 9B shows multi-neuron readings from a rat subject with a branching micro-electrode according to the method of the present invention.
Figure 9C:
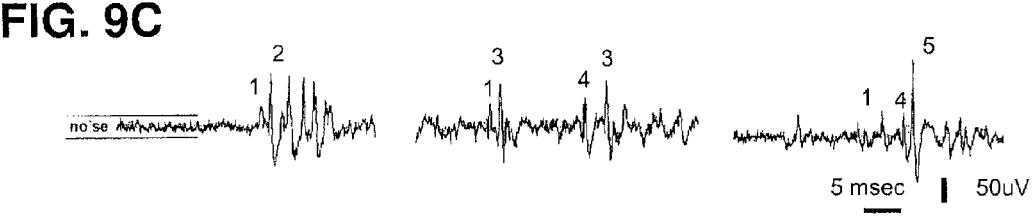
FIG. 9C shows multi-neuron readings for a rat subject taken with a branching micro-electrode according to the method of the present invention.

For example, as shown in FIGS. 9A-9C, EEG readings taken from freely-moving rats in a manner similar to that described above for humans and, using an apparatus substantially the same as that described above, demonstrate the efficacy of therapeutic agents applied to the brain via the subdural delivery strips 102. In particular, FIGS. 9A-9C demonstrate the suitability of branching microelectrodes 114, 116, 118 for long term simultaneous recording of EEG signals as well as multi-neuron recordings. Specifically, FIG. 9A depicts an EEG recording over a period of 2 seconds and a dynamic voltage range of 500 YV, as those skilled in the art will understand. FIGS. 9B and 9C depict multi-neuron recordings taken from the cerebral cortex simultaneously with the EEG of FIG. 9A. FIG. 9C highlights action potentials of five difference neurons recorded from the same microelectrode pair, thereby evidencing the long term efficacy of the system 100 of the present invention in providing multi-neuronal readings. As individual wires of the microelectrodes 114, 116, 118 end in different regions of the neocortex, the arrangement of the present invention allows the recording of multi-neuron activity from a plurality of regions of the brain via a single recording channel, thereby streamlining a monitoring and treatment process of brain electrical activity.

Figure 10A:
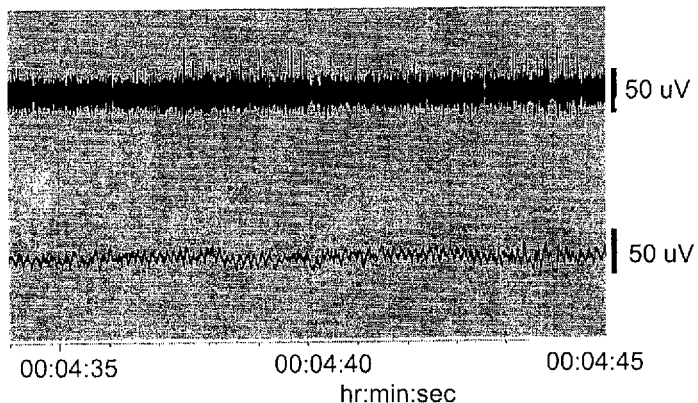
FIG. 10A shows EEG and multi-neuron readings for a rat prior to administration of an epilepsy evoking agent.
Figure 10B:
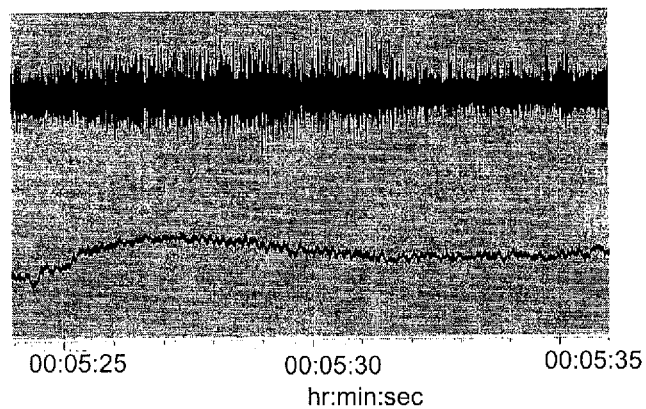
FIG. 10B shows EEG and multi-neuron readings for a rat after administration of an epilepsy evoking agent and prior to the onset of epileptic seizures.
Figure 10C:
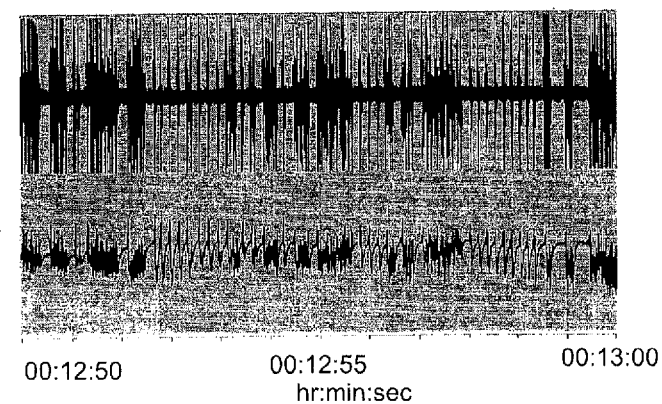
FIG. 10C shows EEG and multi-neuron readings for a rat after administration of an epilepsy evoking agent, indicating a production of epileptic convulsions.

FIGS. 10A-10C depict neuronal activity readings taken from a rat prior to and after the onset of a seizure, thereby demonstrating the utility of continuous monitoring of brain electrical activity. The readings shown in FIGS. 10A-10C have been taken from a freely moving rat provided with a branching microelectrode with 4 branches, each branch having a diameter of 25 Ym and inserted into cortical tissue in accordance with the method of the present invention. Specifically, FIG. 10A depicts readings taken from an immobile rat prior to the administration of epidural kainic acid, which, as those skilled in the art will understand, is an excitatory amino acid receptor agonist used to evoke epileptic seizures in rats. The upper trace of FIG. 10A depicts multi-neuron activity readings from the rat and the lower trace depicts an EEG thereof, wherein both traces are indicative of normal brain electrical activity. Subsequently, 10 mM of kainic acid is delivered onto the dura mater over the parietal cortex of the rat. FIG. 10B depicts the brain electrical activity of the rat 25-35 seconds after delivery of the kainic acid, the upper trace clearly indicating a substantial increase in multi-neuron activity, further indicating an abnormality. The lower trace of FIG. 10B however, does not indicate any abnormalities therein. FIG. 10C depicts brain electrical activity 8 minutes after administration of the kainic acid, which is now causing epileptic convulsions in the rat, wherein both the upper trace and lower trace indicate abnormalities therein. In light of the above, it is noted that the multi-neurons recordings were able to predict the onset of epileptic convulsions well before their onset. Application of this model with the exemplary embodiment of the present invention allows for the administration of a preventative agent directly to an affected area of the brain prior to the onset of epilepsy.

The device of the present invention is tailored for easy integration into therapeutic medical implants (e.g., hybrid neuroprostheses or other analogous devices) that use minipumps for supplying therapeutic agents and flushing fluids to the subdural delivery strip and utilize a microprocessor for analyzing, in real-time, the multi-neuron and EEG signals picked up by the branching microelectrodes of the subdural delivery strips 102. Devices employing the subdural delivery strips 102 of the present invention can be used to treat neocortical disorders such as intractable focal epilepsy, some types of strokes and brain tumors and Alzheimer's disease, symptoms of which are directly related to widespread neocortical synaptic dysfunctions.

Although the present invention is designed ultimately for human use, its applicability should not be limited to use solely on human subjects. For example, the scope of the apparatus and methods of the present invention includes the use of the present invention in animals as a means to test the safety and effectiveness of therapeutic agents on the brain in conjunction with the system of the present invention.

There are many modifications of the present invention which will be apparent to those skilled in the art without departing from the teaching of the present invention. For example, as indicated earlier, any plurality of subdural delivery strips 102 may be employed in a single procedure. Each of the plurality of subdural delivery strips 102 may be delivered either adjacent to one another or, alternatively, to separate areas for the brain 108 predesignated for treatment. Furthermore, each of the plurality of subdural delivery strips 102 may be employed simultaneously or, alternatively, only some of the plurality of subdural delivery strips may operate at a time depending on which targeted area of the brain 108 exhibits abnormal brain activity, as those skilled in the art will understand. The embodiments disclosed herein are for illustrative purposes only and are not intended to describe the bounds of the present invention which is to be limited only by the scope of the claims appended hereto.

What is claimed is:

1. An apparatus for treating the brain, comprising:
   a first fluid delivery device including a distal end sized and shaped for placement at a first target site between a dura mater and a pia mater of the brain, the first fluid delivery device including a first fluid lumen extending along a first fluid lumen path from a first fluid lumen proximal end to a first fluid lumen distal end open to a first outlet opening in the distal end of the first fluid delivery device to deliver fluids to a first target location and a second fluid lumen extending through the first fluid delivery device along a second fluid lumen path from a second fluid lumen proximal end to a second fluid lumen distal end open to the first outlet opening, wherein the first fluid lumen path is separated from the second fluid lumen path; and
   a first microelectrode extending from a microelectrode proximal end to a first distal tip, the first microelectrode being mounted within the distal end of the first fluid delivery device for movement between an insertion position in which a first distal tip of the first microelectrode is received within the first fluid delivery device and a deployed position in which the first microelectrode extends out of the first fluid delivery device with the first distal tip thereof penetrating the pia mater to a first electrode target position in the cerebral cortex, wherein the first microelectrode is movable independently of the first fluid lumen.

2. The apparatus of claim 1, further comprising:
   a second microelectrode extending from the microelectrode proximal end to a second distal tip, the second microelectrode being mounted within the distal end of the first fluid delivery device movable between an insertion configuration in which the second distal tip thereof is received within the first fluid delivery device and a deployed configuration in which the second distal tip of the second microelectrode penetrates the pia mater to a second electrode target position in the cerebral cortex; and
   a third fluid lumen extending through the first fluid delivery device from the first fluid lumen proximal end to a second outlet opening which, when the first fluid delivery device is at the first target site, opens to a second target location.

3. The apparatus of claim 2, further comprising a fourth fluid lumen extending through the first fluid delivery device from the second fluid lumen proximal end to the second outlet opening.

4. The apparatus of claim 3, further comprising:
   a third microelectrode extending from the microelectrode proximal end to a third distal tip, the third microelectrode being mounted within the distal end of the first fluid delivery device movable between an insertion configuration in which the third distal tip thereof is received within the first fluid delivery device and a deployed configuration in which the third distal tip of the third microelectrode penetrates the pia mater to a third electrode target position in the cerebral cortex; and
   a fifth fluid lumen extending through the first fluid delivery device from the first fluid lumen proximal end to a third outlet opening which, when the first fluid delivery device is at the first target site, opens to a third target location.

5. The apparatus of claim 4, further comprising a sixth fluid lumen extending through the first fluid delivery device from the second fluid lumen proximal end to the third outlet opening.

6. The apparatus of claim 5, wherein the third electrode target position corresponds to the third target location.

7. The apparatus of claim 6, wherein the first, third and fifth fluid lumens extend through the first fluid delivery device to a source of therapeutic agent and the second, fourth and sixth fluid lumens extend through the first fluid delivery device to a source of one of artificial cerebrospinal fluid and saline.

8. The apparatus of claim 7, wherein the lengths of the first, second, third, fourth, fifth and sixth fluid lumens are substantially equal to one another.

9. The apparatus of claim 8, wherein the first and second fluid lumens extend along a first winding path to reach the first outlet opening and the third and fourth fluid lumens extend along a second winding path to reach the second outlet opening, each of the first and second winding paths having a length equal to that of a third path along which the fifth and sixth fluid lumens extend to the third outlet opening.

10. The apparatus of claim 7, further comprising a controller analyzing data received from the first, second and third microelectrodes and, when a predetermined target brain activity is detected, supplying to the first, second and third target positions one of a therapeutic agent and a neutral agent.

11. The apparatus of claim 10, wherein the neutral agent includes one of artificial cerebrospinal fluid and saline.

12. The apparatus of claim 4, wherein the first, second and third microelectrodes extend distally from a single branching electrode.

13. The apparatus of claim 4, wherein the first microelectrode further includes a second distal tip which, when in the insertion position, is received within the first fluid delivery device and which, when in the deployed position, extends out of the first fluid delivery device to penetrate the pia mater at a second first electrode target position in the cerebral cortex.

14. The apparatus of claim 13, wherein the first microelectrode further includes a third distal tip which, when in the insertion position, is received within the first fluid delivery device and which, when in the deployed position, extends out of the first fluid delivery device to penetrate the pia mater at a third first electrode target position in the cerebral cortex.

15. The apparatus of claim 4, further comprising a canal formed in the first fluid delivery device to house the first, second and third microelectrodes therein when in the insertion position.

16. The apparatus of claim 15, wherein the canal is formed of one of fused silica and Teflon.

17. The apparatus of claim 15, wherein the canal is angularly shaped to allow the first, second and third microelectrodes to exit at an angle of between 10 degrees to 30 degrees with respect to a surface of the pia mater.

18. The apparatus of claim 4, wherein the first, second and third microelectrodes detect one of an EEG signal and multineuronal activity in the brain.

19. The apparatus of claim 4, further comprising:
   a second fluid delivery device including a distal end sized and shaped for placement at a second target site between the dura mater and the pia mater of the brain, the second fluid delivery device including a seventh fluid lumen extending to a fourth outlet opening in the distal end to deliver fluids to a second target location; and
   a fourth microelectrode mounted within the distal end of the second fluid delivery device for movement between an insertion position in which a first distal tip of the fourth microelectrode is received within the second fluid delivery device and a deployed position in which the fourth microelectrode extends out of the second fluid delivery device with the first distal tip thereof penetrating the pia mater to a first fourth electrode target position in the cerebral cortex.

20. The apparatus of claim 2, wherein the second electrode target position corresponds to the second target location.

21. The apparatus of claim 1, further comprising a laser-perforated disk disposed over an opening of the first outlet opening.

22. The apparatus of claim 21, wherein the laser-perforated disk is formed of an MRI-compatible material.

23. The apparatus of claim 21, wherein the laser-perforated disk comprises 5,000-60,000 perforations.

24. The apparatus of claim 21, further comprising a silicone rim formed around a periphery of the laser-perforated disk, the silicone rim adapted to prevent a spillover of fluids from the perforated disk to non-targeted locations.

* * * * *